United States Patent [19]

Seiler et al.

[11] 4,083,861
[45] Apr. 11, 1978

[54] UNSATURATED SILICON ORGANIC COMPOUNDS CONTAINING KETO GROUPS

[75] Inventors: Claus Dietrich Seiler, Rheinfelden; Hans-Joachim Vahlensieck, Wehr, both of Germany

[73] Assignee: Dynamit Nobel Aktiengesellschaft, Troisdorf, Germany

[21] Appl. No.: 683,160

[22] Filed: May 4, 1976

[30] Foreign Application Priority Data

May 2, 1975 Germany ............................ 2519720

[51] Int. Cl.$^2$ .............................................. C07F 7/18
[52] U.S. Cl. .......................................... 260/448.8 R
[58] Field of Search ................................ 260/448.8 R

[56] References Cited

U.S. PATENT DOCUMENTS

Re. 27,281   2/1972   Wilkus et al. ............. 260/448.8 R X
3,746,734    7/1973   Berger et al. ............. 260/448.8 R X

*Primary Examiner*—Paul F. Shaver
*Attorney, Agent, or Firm*—Burgess, Dinklage & Sprung

[57] ABSTRACT

A keto-group-containing silane of the formula

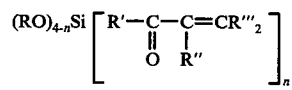

wherein
R independently represents an alkyl, cycloalkyl, alkyloxyalkyl and phenyl group,
R' represents an unsubstituted straight-chained or branched alkylene or alkenyl cycloalkylene or cycloalkenyl group having 2 to 8 carbon atoms,
R" represents a hydrogen atom or an alkyl group having 1 to 4 carbon atoms,
R''' represents a hydrogen atom, a straight-chained or branched alkyl or alkenyl group having 1 to 6 carbon atoms or a $C_5$-$C_6$ cycloalkyl group, and
n has the value 1 or 2, and the condensation products thereof; processes for their production and the use thereof and facilitating the adhesion of inorganic oxidic and metallic surfaces to polyaddition or polycondensation polymeric compositions.

54 Claims, No Drawings

UNSATURATED SILICON ORGANIC COMPOUNDS CONTAINING KETO GROUPS

BACKGROUND OF THE INVENTION

Field of the Invention

This invention relates to novel keto-containing organosilicon compounds, intermediates employed in the preparation of such keto-containing organosilicon compounds, processes for the production of such keto-containing organosilicon compounds and the use of such compounds to improve the adhesion of between inorganic oxidic and metallic surfaces on the one hand and polyaddition or polycondensation polymeric compositions on the other. This invention further relates to siloxanes prepared by hydrolysis of the keto-containing organosilicon compounds of the invention.

SUMMARY OF THE INVENTION

Broadly this invention contemplates a keto-containing organosilicon compound of the general formula:

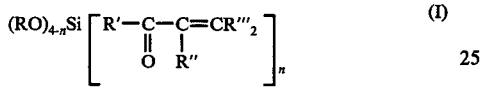
(I)

wherein
- R independently represents an alkyl, cycloalkyl, alkyloxyalkyl and phenyl group,
- R' represents an unsubstituted straight-chained or branched alkylene or alkenyl cycloalkylene or cycloalkenyl group having 2 to 8 carbon atoms,
- R" represents a hydrogen atom or an alkyl group having 1 to 4 carbon atoms,
- R'" represents a hydrogen atom, a straight-chained or branched alkyl or alkenyl group having 1 to 6 carbon atoms or a $C_5$-$C_6$ cycloalkyl group, and
- $n$ has the value 1 or 2, The invention is also concerned with siloxane compositions prepared by hydrolysis of such organosilicon compounds.

It has been discovered in accordance with the invention that the novel organosilicon compounds or their siloxanes provide improved adhesion between an inorganic oxidic or metallic surface on the one hand and a polyaddition or polycondensation polymeric composition on the other. This would be seen from the data in the examples below.

There are several methods by which the novel organosilicon compound can be prepared. One such method involves the reaction of a silane of the formula

(II)

wherein R and $n$ have the meanings given above with compounds of the general formula

(III)

wherein $R^x$ represents a $C_{2-8}$ alkyl, cycloalkyl or branched alkyl radical which contains at least one double or triple bond in the chain and R" and R'" have the same meanings given above. Generally speaking, $R^x$ represents a $C_2$-$C_8$ alkyl, cycloalkyl or branched alkyl radical, especially a $C_2$-$C_4$ alkyl, cycloalkyl or branched alkyl radical. The reaction is carried out in the presence of an inhibitor and a platinum compound catalyst. It can be conducted in the presence or absence of an inert solvent. The reaction is conducted such that the Si-H bond is added to the double bond contained in the $R^x$ moiety with the formation of an Si-C bond.

Typical alkoxysilanes which can be employed in accordance with the invention are trimethoxysilanes, triethoxysilanes, dimethoxysilanes, diethoxysilanes, tri(methoxy-ethoxy)-silanes di(methoxy-ethoxy)silanes, tri(phenoxy)silanes, and di(phenoxy)-silanes.

Typical alkenyl vinyl ketones in accordance with the invention are compounds of the formulas:

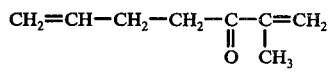

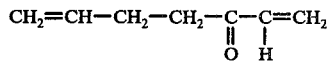

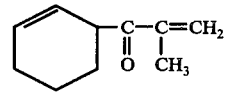

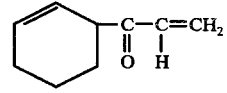

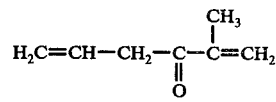

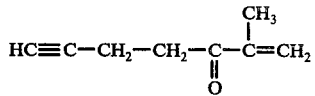

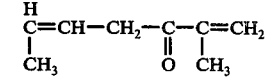

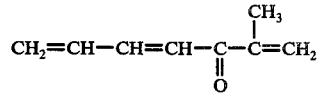

The platinum complexes or compounds employed as catalysts include in particular complex Pt(IV) compounds, such as, for example, $H_2PtCl_6$, platinum-olefin complex compounds, and platinum-mesityl oxide complex compounds. See German Pat. Nos. 1,069,148, 1,165,028, 1,187,240, 1,210,844 and German "Auslegeschrift" 1,937,904, the disclosures of which are hereby incorporated herein by reference. The catalysts disclosed in such patents and Auslegeschrift are also useful in accordance with the process of the present invention. Other catalysts useful include those of the general formula [PtR$^1$Cl$_2$]$_a$ wherein R$^1$ is an unsaturated (olefinically unsaturated) ketone residue and wherein $a$ is 1 or 2. Within this definition are platinum mesityl oxide complex catalysts and catalysts wherein R$^1$ is a moiety derived from butanone, phorone, isophorone, dibenzylacetone and other such unsaturated ketones. Generally speaking the platinum compound or complex catalyst is present in the reaction mixture in an amount of between 0.02 and 0.60 weight percent, preferably between 0.08 and 0.14 weight percent.

The inhibitors which are employed during the reaction are polymerization inhibitors especially olefin polymerization inhibitors. Particularly contemplated polymerization inhibitors include compounds such as hydroquinone, quinone and aminophenol as well as condensed aniline derivatives. Generally speaking the inhibitors present in the reaction mixture are in an amount of between 1.0 and 7.0 weight percent, preferably between 3.5 and 5.0 weight percent.

The reaction was conducted at a temperature between 45° and 130° C, preferably between 85° and 105° C for between 5 and 60 minutes, especially between 35 and 50 minutes. While subatmosphereic and superatmospheric pressures can be employed the reaction was generally conducted at atmospheric pressure. Stoichiometric amounts of the reactants are present although the stoichiometric ratio of silane to keto-containing compound in the range of 0.8 to 1.2:1.

In accordance with another embodiment of the invention the organosilicon compounds of the invention can be prepared by reacting alkoxysilanes of the general formula $$(RO)_{4-n}\text{-SiH}_n \qquad (IV)$$

wherein R and $n$ have the same meanings as set forth above, with compounds of the general formulas:

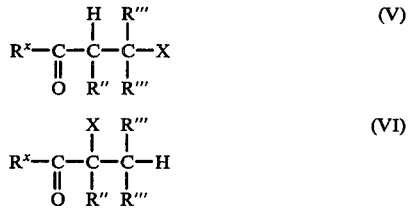

wherein R" and R'" have the same meanings as set forth above and R$^x$ has the same meaning as set forth in Formula III supra and X represents a reactive group which, upon cleavage of HX forms a double bond at the position of X, i.e., a terminal double bond. The process is carried out in the presence or absence of an inert solvent and in the presence of a platinum compound catalyst such as that set forth above. The process is conducted such that the Si-H bond of the alkoxysilane compound is added to one of the double bonds contained in the R$^x$ moiety with the formation of an Si-C bond. As a result thereof there are formed as intermediate compounds compounds of the general formulas:

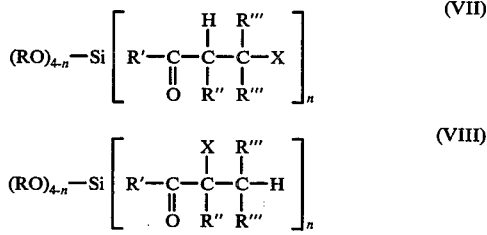

wherein R, R', R", R'" and $n$ have the same meanings as set forth in Formula I and X has the same meaning as set forth in formula VI.

After preparation of these intermediates, with or without their preparation from the reaction mixture they are converted to the keto-containing organosilicon compounds of the invention by removal of the X moiety through a reaction whereby HX is cleaved from the compound resulting in a double bond on the terminal carbon atom. In the formula X can be a any number of a different moiety such as a halogen atom especially chlorine or bromine, an amino group, an alkylamino group, especially a $C_1$-$C_8$ alkylamino group and any one of the following groups. Generally it can be any group which to some extent will form an HX compound leaving a double bond in the terminal carbon atom of the keto-containing organo compound.

Typical alkoxysilanes in the meaning of the invention are, again, compounds such as those set forth above including in particular a trimethoxysilane and triethoxysilane as well as dimethoxydihydrogen silane and diethoxydihydrogen silane. Especially suitable olefinic compounds for the process include the compounds of the following formulas:

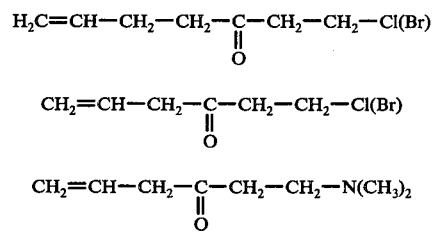

Referring to the formulas above the moiety X is preferably a halogen or a tertiary amine especially a tertiary $C_1$-$C_8$ alkylamine. However, it can also represent an acetyl group or another group which enters into a β-elimination reaction.

Catalysts employed for the preparation of the intermediate compound include the platinum catalyst as set forth above. Platinum-hydrochloric acid in alcoholic solution is a preferred platinum catalyst for the performance of the addition reaction (Si-H onto -C=C). The reaction is conducted at a temperature between 45° and 130° C, but mostly in the range of 70° to 105° C. While subatmospheric and superatmospheric pressures are employed the reaction is generally performed at atmospheric pressure. The reaction is generally conducted for a period of time of between 5 and 60 minutes, especially between 35 and 50 minutes employing stoichiometric amounts of the reactants. However, the silane can be in a molar excess or deficiency relative to the X moiety containing organo compound and thus in a molar ratio with respect thereto of 0.8 to 12:1.

Following the synthesis of the intermediate compound an H-X cleavage reaction occurs. The intermediate need not be separated from the reaction mixture and can be cleaved in the reaction mixture although in some instances it is preferred to separate the intermediate from the reaction mixture. Cleavage is effected employing an H-X cleavage reagent which will remove the X moiety and cause it to unite with the hydrogen of the keto-containing intermediate resulting in the formation of a double bond in the terminal carbon atom. Typical reagents for the cleavage include alkaline substances especially alcoholates and in particular alkali metal $C_1$-$C_8$ alcoholates or phenolates (e.g., potassium tert.-butanolate) a phenolate or an amine. Particularly contemplated amines include dicyclohexylethylamine, dicyclohexylmethylamine, diethylaniline and dimethylaniline. The cleavage is performed in known manner at normal or elevated temperatures, usually at a temperature in the range of 25° to 100° C. The cleavage agent is contacted with the intermediate compound in a stoichiometric amount. Generally speaking there are between 1.3 and 1 moles of cleavage agent per mole of intermediate. The process can be conducted at atmospheric pressure, subatmospheric pressure or superatmospheric pressure although the pressure generally lies within the range of 0.9 to 1.1 atmospheres.

In accordance with the invention there is still another method for the preparation of the keto-containing organosilicon compounds of the invention which comprises contacting an organosilane of the formula

  (IX)

wherein R and n have the same meanings as in Formula I and $R^{IV}$ represents a straight-chained or branched alkenyl group of 2 to 8 carbon atoms, especially a straight-chained or branched chained alkenyl group of 2 to 4 carbon atoms or a cycloalkenyl group of 5 to 6 carbon atoms with compounds of the general formula

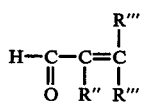  (X)

wherein R'' and R''' have the meaning given in Formula I by radical addition, to form compounds of the type:

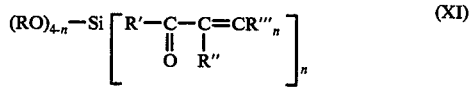  (XI)

Typical compounds of Formula IX in the meaning of the invention are vinyl trimethoxysilane, allyltrimethoxysilane, and butene-(3)-yl-trimethoxysilane, which are prepared by known methods.

Typical compounds of Formula X in the meaning of the invention are acrolein and methacrolein or crotonic aldehyde. Others include ethylacrolein and methylethylacrolein.

The reaction is performed in the presence of UV-rays or a radical forming agent. The radical forming agents are generally present in a reaction mixture in an amount of between 0.5 and 2% by weight, preferably between 0.9 and 1.3% by weight. A wide variety of radical forming agents can be employed including in particular peroxide radical forming agents of which dibenzoyl peroxide, diacetyl peroxide and ditert.-butyl peroxide are especially suitable.

The reaction can be performed, again, in the presence or absence of an inert media. Where the reaction is performed in the presence of an inert media hexane and cyclohexane are particularly useful. The reaction is conducted at a temperature of between 25° and 75° C, preferably between 40° and 50° C at a pressure between 1.1 and 0.9 atmospheres. The reaction is conducted for between 60 and 500 minutes, it being desirable to maintain the specific reaction temperatures.

In like manner, as stated in the preceding paragraphs, the compounds of the invention are also formed by the radical addition of compounds of the general formulas

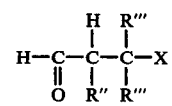  (XII)

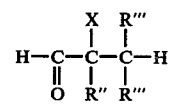  (XIII)

onto compounds of Formula IX.

Typical compounds of Formulas XII and XIII in the meaning of the invention are 3-chloropropanal-1, 2-chloropropanal(1) and 3-chloro-2-methylpropanal(1).

The compounds of the following general formulas:

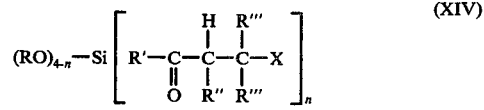  (XIV)

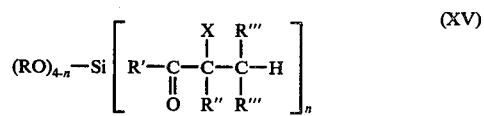  (XV)

wherein R, R', R'', R''' and n have the same meaning as in Formula I and X has the meaning given in Formula VI are then transformed in an inert medium into the products of the invention by HX cleavage.

When preparing compounds of the invention employing a keto compound of the Formula XII or XIII a two-step process is involved initially involving an addition reaction and thereafter an HX cleavage. The addition reaction can be performed using the same process paramaters applicable to the preparation of compounds of the invention by the reaction of an organosilicon compound of Formula IX with a keto-containing organo compound of Formula X. The preferred radical forming agents are UV-rays.

Again, the process can be conducted in the presence or absence of an inert media. An inert media, however, is desirable under certain circumstances to distribute the temperature evenly. Inert media which are particularly suitable include a hydrocarbon such as hexane or benzene.

In the cleavage reaction the cleavage agents set forth above are also useful including in particular alcoholates, for example, alkali metal alcoholates of $C_1$-$C_8$ monoalkanols such as sodium methylate, tertiary amines such as triethylamine, or diethylaniline. Other tertiary $C_1$-$C_8$ alkylamines are also useful.

It is preferred to perform the reaction in the presence of a polymerization inhibitor in order to reduce the polymerization of the compounds of the invention. For this reason the polymerization inhibitors are set forth above in the use of the reactants of Formula III can also be employed. Particularly suitable polymerization inhibitors include aminophenols and hydroquinone. When employed the polymerization inhibitors are present in an amount of between 0.1 and 2.0% by weight, preferably between 0.4 and 1.4% by weight, based upon the weight of the reaction mixture.

The desired product is recovered by a work-up procedure involving the use of vacuum distillation with the addition of polymerization inhibitors such as in an amount between 0.2 and 0.6% by weight based upon the weight of the mass charged to the vacuum still. The vacuum is desirably quite high, preferably better than 1.5 Torr so that the distillation can be performed at the lowest possible temperature.

In accordance with this invention there is provided still another method for the preparation of the organosilicon compounds of the invention. In this embodiment there is provided a simple method if the compounds which are reacted are not aldehyde compounds but compounds of the general formula

(XVI)

wherein Z' represents a halogen atom and R" and R'" have the same meaning as set forth above in respect of Formula I. These are reacted with compounds of the general formula

(XVII)

wherein $n$ has the meaning set forth as in Formula I, $R^{IV}$ has the meaning as in Formula IX and Z represents a halogen or an alkoxy group, e.g., $C_1$-$C_6$ alkoxy group.

This reaction is performed in the presence of a Friedel-Crafts catalyst and involves the addition of the carboxylic acid halides. As a result there is formed primarily β-halogen ketones or unsaturated ketones. Usually, however, the unsaturated ketones are formed under the influence of the Friedel-Crafts catalyst. By carefully working, however, one can isolate the β-halogen ketones.

Friedel-Crafts catalysts useful for this addition reaction include in particular aluminum chloride, tin(IV), chloride, zinc chloride and titanium (IV) chloride. The process can be conducted in the presence or absence of a solvent. If conducted in the presence of a solvent dichloromethane, dichloroethane, tetrachloromethane, carbon tetrachloride, hexane and heptane, among others, are useful. The process is conducted at temperatures around 0° C but temperatures above and below 0° C are also useful. Generally, the temperature is in the range of −10° to +20° C, preferably −5° to +5° C.

Following the addition reaction the Z moiety is replaced through a standard esterification reaction. When chloroalkenyl silanes are used as starting materials, work-up of the compounds of the invention is performed by separating the β-halogen ketones or unsaturated ketones, as the case may be, from the medium containing the catalyst and then subjecting them to a conventional esterification. However, one can perform the esterification likewise in the catalyst-containing medium. The method of procedure permits an especially easy separation of the catalyst from the compounds of the invention, since the latter are concentrated in the inert organic solvents in which the Friedel-Crafts synthesis was performed while the catalyst remains in the predominantly alcoholic second phase of the esterification.

The esterification is performed with the alcohol which can provide the desired R group on the unsaturated silicon organic compound to be prepared. Since R represents a $C_1$-$C_6$ alkyl, cycloalkyl, $C_3$-$C_8$ alkoxyalkyl or phenol group the alcohol employed for the esterification will be a $C_1$-$C_6$ alkanol or a cycloalkanol, a $C_3$-$C_8$ alkoxyalkanol or a phenol, especially phenol itself.

In accordance with still a further embodiment of the invention compounds of the present invention can be prepared by the reaction of the compound of the formula

(XVIII)

wherein $n$ has the meaning given above in respect of Formula I, $R^{IV}$ has the same meaning as in Formula IX and Z has the same meaning as given in Formula XVII with compounds of the general formulas:

(XIX)

(XX)

wherein R" and R'" have the same meaning as in Formula I, X has the same meaning as in Formula VI and Z' has the same meaning as given in Formula XVI. The use of these reactants consistutes a special variant of the procedure. The initial reaction is conducted at a temperature between −10° and +20° C, preferably between −5° and +5° C and forming a pressure between 1.2 and 0.8 atmosphere, especially atmospheric pressure. The reaction again takes place in the presence of a Friedel-Crafts catalyst in the presence or absence of an inert solvent. The Friedel-Crafts catalyst is present in an amount of between 16 and 28 weight percent, especially between 20 and 24 weight percent. These concentrations of catalysts are also useful in the reaction described supra between silanes of the Formula XVII and a keto-containing compound of Formula XVI. Friedel-Crafts catalysts useful for this latter variant are the same Friedel-Crafts catalysts useful for the reaction between the keto compound of Formula XVI and the silane of the compound of Formula XVII. Solvents which can be employed include those solvents listed above, particularly dichloroethane and tetrachloroethane. The reactants are present in a stoichiometric amount although the molar ratio of silane to keto compound can be in the range of 0.9 to 1.1 : 1.

Depending upon the keto compound selected there will be provided an α or β-halogen ketone as an intermediate which will have one of the following formulas:

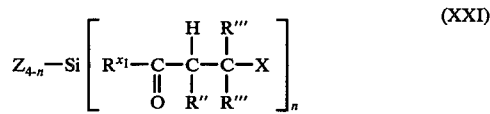

(XXI)

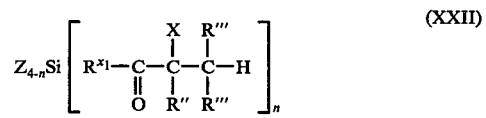

(XXII)

wherein R", R'" and $n$ have the same meaning as in Formula I, Z has the same meaning as in Formula XVII, X has the same meaning as in Formula VI, and $R^{x'}$ represents a halogenated alkylene, cycloalkylene or branched alkylene group which can contain one or more or no double bonds or triple bonds. After the preparation of the α or β-halogen ketones the esterification reaction can be employed using the above-named esterification alcohols. As in the esterification discussed above the reaction is conducted employing a stoichiometric amount of alcohol especially a molar excess up to about 10%. Esterification is conducted at a temperature between 30° and 90° C at a pressure of between 0.7 and 1.0 atmospheres. Generally the esterification is conducted until there is no further evidence of evolution of halogen compound or alcohol (derived from a compound wherein Z is an alkoxy group).

The esterification was therefore followed by the cleavage of components HX and HZ' with the aid of alkalies such as those set forth above whereby there is formed compounds of the general formula

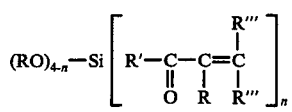
(XXIII)

wherein R, R', R", R''' and $n$ have the meaning set set forth in Formula I.

Alternatively the compounds of XXII can be prepared by the esterification of the halogen ketones in the reaction mixture followed by cleavage of the components HX and HZ' in a single reaction step by reaction with alkalies, without separation of the trialkoxysilyl halogen ketones. The alkali is particularly useful for this step include those compounds set forth above including in particular sodium methylates, triethylamine, diethylaniline and dicyclomethylamine.

The reaction is performed, depending upon the ease of cleavage of the components HX and HZ', at temperatures between 25° and 100° C. To prevent a parallel polymerization of the compounds it is recommended to perform the cleavage reaction in the presence of polymerization inhibitors such as condensed anilines, aminophenols and hydroquinone. These are generally employed in an amount between 0.1 and 2.0 weight percent, based uon the weight of the reaction mixture.

The compounds of the invention are substances which are characterized by the grouping

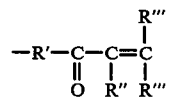

wherein R', R" and R''' have the same meaning as in Formula I, and they are especially suitable for incorporation by polymerization into other unsaturated compounds. Such compounds are olefins of all kinds, especially unsaturated polyesters.

Since the compounds of the invention also contain a trialkoxysilyl or dialkoxysilyl grouping, they are also susceptible of entering into compounds with the oxidic surfaces of inorganic substances. Such inorganic substances are, for example, glass, glass fibers, glass spheres, mica sands, $Al_2O_3$, asbestos $SiO_2$, $TiO_2$, calcium silicate, iron oxides, calcium carbonate or mixtures thereof. When recovered the silanes can be included in a polyaddition or polycondensation polymeric composition in an amount amounting to from 0.05 to 5 weight percent. Amounts above and below this quantity are also contemplated. The silicon compounds are used as additives to binding agents comprising polycondensation products such as phenol-formaldehyde and furan resins, aminoplastics or polyaddition polymers. Examples of such polyaddition products known to be used as binding agents are epoxy resins, urethane resins and polyester resins. The polycondensation products include cold-setting and/or thermosetting phenol-formaldehyde resins. The silicon compounds of the present invention can be used to improve the bonding characteristics of all such materials.

Bonding to the inorganic substances can be effected by hydrolyzing the compounds of the invention and applying the hydrolyzates to the inorganic surfaces. When hydrolysis is effected there is formed a siloxane. Hydrolysis is effected by contacting the organosilicon compound with an acid or a base such as in an amount of between 0.1 and 1.0 weight percent.

The adhesion improvement can also be performed by applying the compounds of the invention either as they are or dissolved in other substances such as alcohols or hydrocarbons to the inorganic substance and then completing the hydrolysis and thereby simultaneously bonding them to the inorganic medium. The inorganic substances thus prepared can be embedded in the organic resins of various kinds and, after appropriate treatment, such as polymerization, they yield substances of much higher strength than unprepared materials or materials prepared with conventional substances such as methacryloxypropyl trialkoxysilanes. The silanes of the invention are accordingly especially well suited for the preparation of foundry sands in which the above-named polyaddition or polycondensation products are employed as binding agents.

Thus, in comparison to products such as γ-methacryloxypropyl trimethoxysilane, increases in bending strength of as much as 30% after 72 hours of boiling have been obtained with the compounds of the invention when the latter were used in the preparation of glass fibers which were added to plastics (polyester resins). This effect illustrates and specialty of the compounds of the compounds of the invention.

One can also add the compounds of the invention directly to the organic resins and, after the incorporation of inorganic substances, perform the polymerization. The effects achieved are equal to those described above.

In order to more fully illustrate the nature of the invention and the manner of practicing the same the following examples are presented.

EXAMPLES

EXAMPLE 1

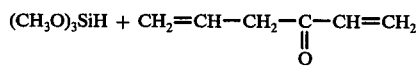

233 g of a mixture consisting of 122 g (1 mole) of trimethoxysilane, 96 g (1 mole) of allyl vinyl ketone, 10 g of hydroquinone and 5 ml of a platinum catalyst (19 ml of isopropanol + 1 g $H_2PtCl_6 \cdot 6 H_2O$) was allowed to flow, at a temperature of 75°-80° C, with vigorous stirring, into a double-walled 2-liter three-necked flask heated by means of a controllable thermostat and equipped with a reflux condenser and dropping funnel, over a period of 25 minutes. After the mixture had been allowed to react for another 15 minutes, it was distilled in vacuo.

At a temperature of 80° C and a pressure of 1.5 Torr, a colorless liquid passed over (62 g), whose molecular weight was determined to be 217, and which had a refractive index of 1.4285 at 25° C. Infrared analysis gave the structure:

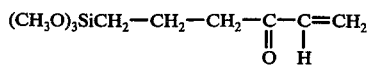

EXAMPLE 2

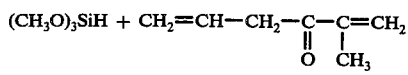

248 g of a mixture consisting of 122 g (1 mole) of trimethoxysilane, 110 g (1 mole) of allyl-α-methylvinylketone, 10 g of hydroquinone and 5 ml of the catalyst described in Example 1 was allowed to flow with vigorous stirring, at a temperature of about 73° to 75° C, into the apparatus described at Example 1, over a period of 30 minutes. The reaction was allowed to continue for 30 minutes at 80° C, and then the mixture was distilled in vacuo.

At 82° C and at a pressure of 1.0 Torr, a colorless liquid passed over (101 g) whose molecular weight was determined to be 231, and which had a refractive index of 1.4230 at 25° C. Infrared analysis gave the structure:

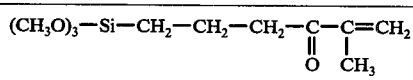

| Elemental Analysis: | C | H | O | Si |
|---|---|---|---|---|
| Theoretical | 51.7 | 8.6 | 27.6 | 12.05 |
| Found | 51.4 | 8.4 | 27.8 | 12.15 |

EXAMPLE 3

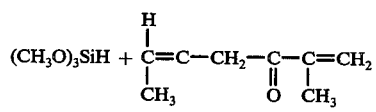

In the apparatus described in Example 1, 261 g of a mixture consisting of 122 g (1 mole) of trimethoxysilane, 124 g (1 mole) of α-methylvinyl-γ-methylallylketone, 10 g of hydroquinone and 5 ml of the catalyst described in Example 1, was made to react over a period of 35 minutes at a temperature of 85° to 90° C. After an after-reaction of 10 to 15 minutes, the reaction mixture was distilled.

At a temperature of 86° C and a pressure of 1.0 Torr, a colorless liquid (85 g) passes over, whose molecular weight is determined at 246, and which has a refractive index of 1.4200 at 25° C. Infrared analysis of the compound gives the structure:

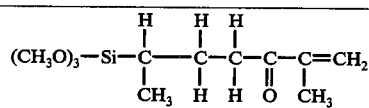

| Elemental Analysis: | C | H | O | Si |
|---|---|---|---|---|
| Theoretical | 53.6 | 8.94 | 26.0 | 11.70 |
| Found | 53.3 | 8.74 | 25.7 | 11.80 |

EXAMPLE 4

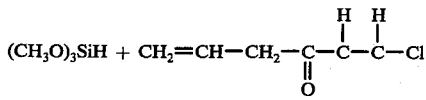

a. In the apparatus described in Example 1, 259.5 g of a mixture consisting of 122 g (1 mole) of trimethoxysilane, 132.5 g (1 mole) of allyl-β-chloroethylketone, 10 g of ditertiary-para-cresol, and 5 ml of the catalyst described in Example 1 was made to react over a period of 40 minutes at 70° to 75° C with vigorous stirring. The mixture was allowed to after-react for 15 minutes, and it was then vacuum distilled.

At a temperature of 92° C and a pressure of 1.0 Torr, 180 g of a colorless liquid passed over, whose molecular weight was determined at 254 and which, upon infrared analysis, had the structure:

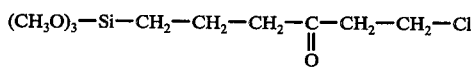

b. 150 g (1 mole) of N,N-diethylaniline, 20 g of hydroquinone and 1 liter of benzene were added to 254 g (1 mole) of the compound obtained in Example 4a) and the mixture was then refluxed at 80° C for 3 hours. After cooling, the hydrochloride was separated by filtration, the filtrate was treated with 5 g of an antioxidant on a basis of diphenyl phenylene diamine (commercially obtainable under the name Nonox DPPD as a product sold by ICI), and was distilled. At a temperature of 80° C and a pressure of 1.5 Torr, a colorless liquid (130 g) passes over, whose molecular weight was determined to be 218 and whose index of refraction is 1.4285 at 25° C. Infrared analysis of the substance gave the structure:

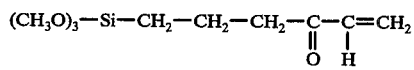

It is identical with the substance obtained in Example 1.

EXAMPLE 5

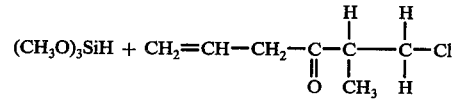

a. 284 g of a mixture consisting of 122 g (1 mole) of trimethoxysilane, 147 g (1 mole) of allyl-(α-methyl-β-chloroethyl)-ketone, 10 g of hydroquinone and 5 ml of the catalyst specified in Example 1 was allowed to flow over a period of 40 minutes into the apparatus described in Example 1, and reacted with vigorous stirring at 68° to 73° C. The reaction mixture was then processed by distillation.

At a temperature of 92° C and a pressure of 1.5 Torr, 200 g of a colorless liquid passed over, whose molecular weight was determined to be 268. Infrared analysis confirmed the following structure for the compound:

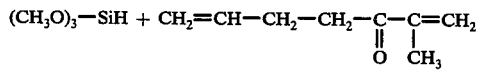

| Elemental analysis: | C | H | O | Si | Cl |
|---|---|---|---|---|---|
| Theoretical | 44.6 | 7.8 | 23.8 | 10.4 | 13.2 |
| Found | 44.3 | 7.6 | 24.2 | 10.3 | 13.2 | b. 150 g (1 mole) of N,N-diethylaniline, 20 g of hydroquinone and 1 liter of benzene were added to the compound obtained under Example 5a) (269 g, 1 mole). Then the mixture was refluxed for 3 hours at about 80° C. After the reaction mixture had cooled and the hydrochloride had been removed by filtration, 5 g of Nonox was added to the filtrate and the latter was vacuum distilled.

At a temperature of 85° C and a pressure of 1 - 2 Torr, a colorless liquid (139 g) passed over, whose molecular weight was determined to be 232 and whose infrared analysis confirmed the following structure:

(CH₃O)₃—Si—CH₂—CH₂—CH₂—C—C=CH₂
                                    ‖  |
                                    O  CH₃

| Elemental analysis: | C | H | O | Si |
|---|---|---|---|---|
| Theoretical | 51.8 | 8.65 | 27.5 | 12.1 |
| Found | 51.6 | 8.55 | 27.7 | 11.9 |

EXAMPLE 6

(CH₃O)₃—SiH + CH₂=CH—CH₂—CH₂—C—C=CH₂
                                           ‖  |
                                           O  CH₃

261 g of a mixture consisting of 122 g of trimethoxysilane, 124 g of (α-methylvinyl)-(n-butene-(3)-yl)-ketone, 10 g of hydroquinone, and 5 ml of the catalyst mentioned in Example 1, was allowed to run into the apparatus described in Example 1 over a period of 35 minutes, with vigorous stirring, at a temperature of 75° to 78° C. After-reaction was allowed to continue for 10 to 12 minutes and then the reaction mixture was processed by distillation.

At 85° C and a pressure of 1 Torr, a colorless liquid (121 g) passed over, whose molecular weight was determined to be 246. Infrared analysis showed the following structure for the product:

(CH₃O)₃—SiCH₂—CH₂—CH₂—CH₂—C—C=CH₂
                                             ‖  |
                                             O  CH₃

| Elemental analysis: | C | H | O | Si |
|---|---|---|---|---|
| Theoretical | 53.6 | 8.9 | 26.1 | 11.4 |
| Found | 53.4 | 8.9 | 26.3 | 11.5 |

EXAMPLE 7

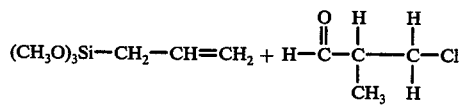

Into the apparatus described in Example 1, additionally equipped with an ultraviolet lamp, there was placed a mixture consisting of 318 g (3 moles) of α-methyl-β-chloropropanal-(1) and 172 g of allyltrimethoxysilane and having a temperature of 20° C. The ultraviolet irradiation was sustained over a period of 35 hours. Thereafter the reaction liquid was processed by distillation.

At a temperature of 95° C and a pressure of 2 - 3 Torr, a colorless liquid passed over, whose molecular weight was determined to be 280. Infrared analysis gives the structure:

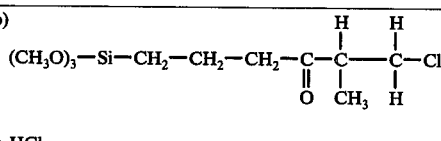

| Elemental analysis: | C | H | Si | Cl | O |
|---|---|---|---|---|---|
| Theoretical | 44.6 | 7.8 | 10.4 | 13.2 | 23.9 |
| Found | 44.3 | 7.7 | 10.5 | 13.3 | 24.1 | b)

(CH₃O)₃—Si—CH₂—CH₂—CH₂—C—C——C—Cl
                                         ‖  |   |
                                         O  CH₃ H $\xrightarrow{-HCl}$ (CH₃O)₃—Si—CH—CH—CH—C—C=CH₂
                                              ‖  |
                                              O  CH₃

150 g (1 mole) of N,N-diethylaniline, 5 g of Nonox and 1 liter of benzene were added to the substance obtained in Example 7a) (278 g, 1 mole). Then the mixture was refluxed at about 80° C for 3 hours. After the mixture has cooled and the hydrochloride that had formed has been removed by filtration, the filtrate was vacuum distilled.

At a temperature of 81° C and a pressure of 1 Torr, 150 g of a colorless liquid passed over, whose molecular weight was determined to be 231, and whose infrared analysis gave the following structure:

(CH₃O)₃—Si—CH₂—CH₂—CH₂—C—C=CH₂
                                         ‖  |
                                         O  CH₃

| Elemental Analysis: | C | O | H | Si |
|---|---|---|---|---|
| Theoretical | 51.7 | 27.6 | 8.6 | 12.1 |
| Found | 52.4 | 27.8 | 8.5 | 12.3 |

EXAMPLE 8

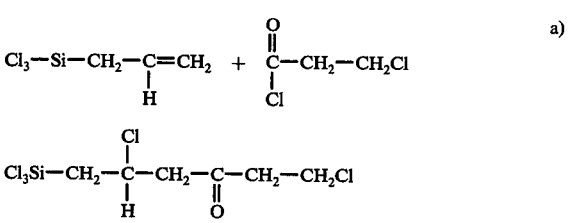

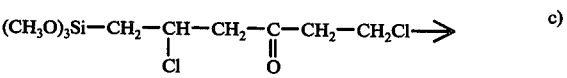

-continued

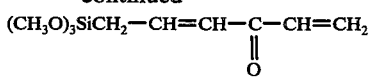

a. In a double-walled 3-liter three-necked flask equipped with stirrer, a reflux condenser and a dropping funnel, 127 g (1 mole) of 3-chloropropanic acid chloride was added to 1.3 moles of $Al^{(III)}Cl_3$ in 200 ml of dichloromethane, at 0° C. Then over a period of 2 hours 175.5 g (1 mole) of allyl trichlorosilane was added drop by drop, the temperature rising to 18° C.

b)

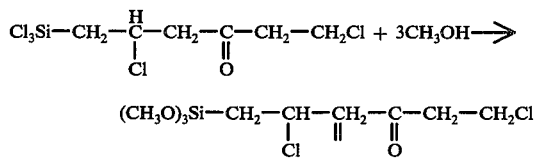

After the reaction had ended, 300 ml of methanol was poured into the dropping funnel and let in, drop by drop, over a period of 4 hours. When the formation of HCl ended, the boiling was continued for another 2 hours at 70° C.

The remaining acidity was neutralized with ammonia and the ammonium chloride thus formed was removed by filtration. The reaction mixture separated upon standing into two phases; the lower phase was used in the further procedure.

c. $(CH_3O)_3Si\text{-}CH_2$

The solution was placed in a 2-liter flask equipped with a fractionating column and, using a water jet vacuum (approx. 30 Torr), the dichloromethane was removed by distillation. 750 ml of benzene, 242 g (2 moles) of dimethyl aniline and 10 g of hydroquinone were added to the residual product. After 4 hours of refluxing, the mixture was cooled, the dimethylaniline hydrochloride was removed by filtration, and the filtrate was vacuum distilled. At 78° C and a pressure of 1 Torr, a colorless liquid distilled over, which had a molecular weight of 216 and a refractive index of 1.4227 at 25° C, and according to infrared analysis had the structure:

| $(CH_3O)_3Si\text{-}CH_2\text{-}CH=CH\text{-}\underset{O}{\overset{\|}{C}}\text{-}\underset{H}{\overset{\|}{C}}\text{-}CH_2$ | | | | |
| --- | --- | --- | --- | --- |
| Elemental analysis: | C | H | O | Si |
| Theoretical | 50.0 | 7.4 | 29.6 | 12.95 |
| Found | 50.3 | 7.3 | 29.4 | 12.7 |

EXAMPLE 9

Styrene was treated with 0.5 wt.-% of a silane of the formula

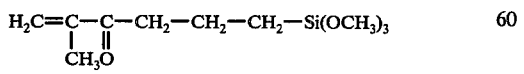

and with 0.3 wt.-% of diacetyl peroxide, and was polymerized onto a degreased glass plate by placing it for 15 hours in a drying oven at temperatures of 100° C.

The polymer thus obtained adhered more strongly than a polymer to which no silane has been added. Even after soaking in water for 6 hours at 50° C, the bond remained unaltered.

EXAMPLE 10

Unsized glass threads were immersed in an 0.25% methanolic solution of a silane of the formula

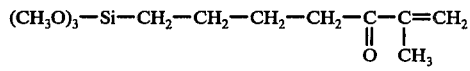

and then dried for 25 minutes in a drying oven at 125° C. The treated threads were wetted heavily with an unsaturated polyester resin, drawn into 4-mm glass tubes, and then set for 2½ hours at 110° C. Upon the removal of the round rods from the tubes, they were cured for another 12 hours at 135° C and the bending strength was determined pursuant to DIN 53,452.

At the same time, the bending strengths were measured of specimens that had been soaked for 72 hours in boiling water.

The same tests were performed using γ-methacryloxypropyltrimethoxysilane as the silane component.

| Silane in the size % | Bending strength of glass fiber reinforced, unsaturated polyester round rods in kp/cm² | |
| --- | --- | --- |
| | Dry | Wet |
| 0.25% Γ-methacryloxy-propyltrimethoxysilane | 11,000 | 7,300 |
| 0.25% α-methylvinyl-δ-butenyltrimethoxy-silyl ketone | 12,700 | 9,500 | kp = kiloponds

EXAMPLE 11

In accordance with the specifications given in Example 10, glass fiber reinforced, unsaturated polyester round rods were made using 0.5% solutions of a silane of the following formula

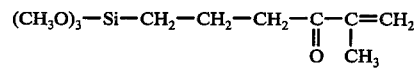

and the following bending strengths were measured:

| Dry: | 11,900 kp/cm² |
| --- | --- |
| Wet: | 10,100 kp/cm² |

EXAMPLE 12

Water-sized glass fibers were wetted as in Example 1 with unsaturated polyester resins to which 0.5% of a silane of the formula

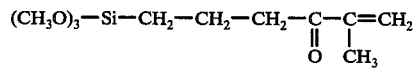

had been added, and were made into glass fiber reinforced, unsaturated polyester resin rods of round cross section. The bending strengths were as follows:

| Dry | 12,000 kp/cm² |
| --- | --- |
| Wet | 9,900 kp/cm². |

What is claimed is:

1. Keto-group-containing silanes of the general formula

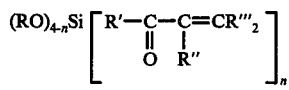

wherein
R independently represents an alkyl, cycloalkyl, alkyloxyalkyl and phenyl group,
R' represents un unsaturated alkenyl, cycloalkylene or cycloalkenyl group having 2 to 8 carbon atoms,
R" represents a hydrogen atom or an alkyl group having 1 to 4 carbon atoms,
R'" represents a hydrogen atom, a straight-chained or branched alkyl or alkenyl group having 1 to 6 carbon atoms or a $C_5$-$C_6$ cycloalkyl group, and
n has the value 1 or 2
and the condensation products thereof.

2. A compound according to claim 1 having the formula

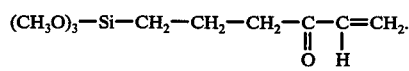

3. A compound according to claim 1 having the formula

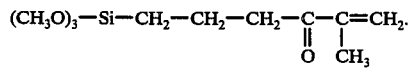

4. A compound according to claim 1 having the formula

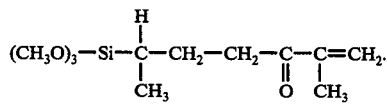

5. A compound according to claim 1 having the formula

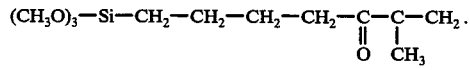

6. A compound according to claim 1 having the formula

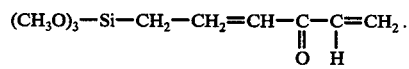

7. A compound of the formula

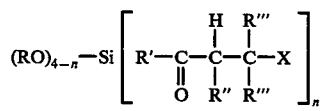

wherein
R independently represents an alkyl, cycloalkyl, alkyloxyalkyl and phenyl group,
R' represents an unsaturated alkenyl, cycloalkylene or cycloalkenyl group having 2 to 8 carbon atoms,
R" represents a hydrogen atom or an alkyl group having 1 to 4 carbon atoms,
R'" represents a hydrogen atom, a straight-chained or branched alkyl or alkenyl group having 1 to 6 carbon atoms or a $C_5$-$C_6$ cycloalkyl group, and
n has the value 1 or 2, and
X is a halogen atom, a tertiary amine group or an acetyl group.

8. A compound according to claim 7 having the formula

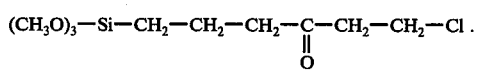

9. A compound according to claim 7 having the formula

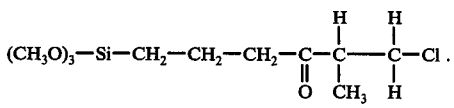

10. A compound of the formula

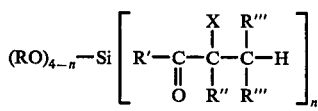

wherein
R independently represents an alkyl, cycloalkyl, alkyloxyalkyl and phenyl group,
R' represents an unsaturated alkenyl, cycloalkylene or cycloalkenyl group having 2 to 8 carbon atoms,
R" represents a hydrogen atom or an alkyl group having 1 to 4 carbon atoms,
R'" represents a hydrogen atom, a straight-chained or branched alkyl or alkenyl group having 1 to 6 carbon atoms or a $C_5$-$C_6$ cycloalkyl group, and
n has the value 1 or 2.

11. A compound according to claim 1 wherein $n = 1$.

12. A process for preparing the compound of claim 1 which comprises contacting a silane of the formula

where R and n have the meaning given in claim 1, with a compound of the formula

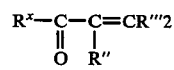

wherein $R^x$ represents a $C_{2-8}$ alkyl, cycloalkyl or branched alkyl radical, containing at least one double or triple bond in the chain, R" and R'" have the meaning given in claim 1 in the presence of a polymerization inhibitor and a platinum compound.

13. A process according to claim 12 wherein the reaction is conducted at a temperature between 45° and 130° C.

14. A process according to claim 12 wherein the reaction is conducted in the presence of a solvent.

15. A process according to claim 12 wherein the reaction is conducted in the absence of a solvent.

16. A process according to claim 12 wherein the silane is selected from the group consisting of trimethoxysilane, triethoxysilane, dimethoxysilane and diethoxysilane.

17. A process according to claim 12 wherein the silane reacts with a compound selected from the group consisting of

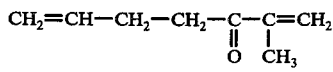

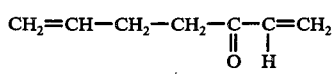

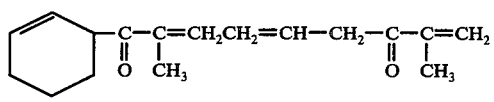

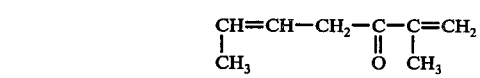

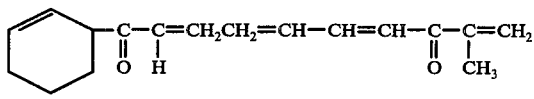

or 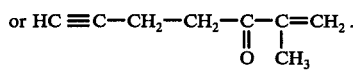

18. A process according to claim 12 wherein the platinum compound is a Pt(IV) complex.

19. A process according to claim 18 wherein the Pt-complex is selected from the group consisting of $H_2PtCl_6$, a platinum-olefin complex compound and a platinum mesityl oxide complex compound.

20. A process according to claim 18 wherein said polymerization inhibitor is selected from the group consisting of hydroquinone, quinone, an aminophenol or a condensed aniline derivative.

21. A process according to claim 18 wherein the Pt-complex is present in the reaction mixture in an amount of between 0.02 and 0.60 weight percent of the component of the reaction mixture and the polymerization inhibitor is present in an amount of between 1.0 and 7.0 weight percent based on the weight of the reaction mixture.

22. A process for producing a compound of claim 1 which comprises contacting a silane of the formula

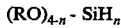

wherein R and $n$ have the same meaning given in claim 1 with a compound of the formula

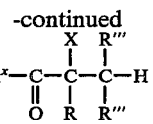

or

-continued

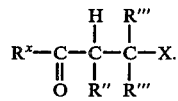

wherein $R^x$ represents a $C_2$-$C_8$ alkyl, cycloalkyl or branched alkyl radical having at least one double or triple bond in the chain, R, R" and R'" have the meaning given in claim 1 and X is a halogen atom, a tertiary amine or an acetyl group in the presence of a platinum compound and thereafter subjecting the resultant compound to H-X cleavage conditions.

23. A process according to claim 22 wherein the silane is reacted with a compound of the formula

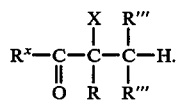

24. A process according to claim 22 wherein the silane is reacted with a compound of the formula

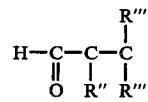

25. A process according to claim 22 wherein the reaction is conducted at 45° to 130° C.

26. A process according to claim 22 wherein the reaction is conducted at 70° to 105° C.

27. A process according to claim 25 wherein HX cleavage is effected by contacting the HX containing compound with an alkaline substance.

28. A process according to claim 27 wherein said alkaline substance is selected from the group consisting of an alcoholate, phenolate or amine.

29. A process according to claim 28 wherein the alkaline substance is an alkaline metal $C_{1-8}$ alcoholate, an alkali metal phenolate or an amine selected from the group consisting of dicyclohexylethylamine, dicyclohexylmethylamine, diethylaniline and dimethylaniline.

30. A process according to claim 29 wherein the cleavage is conducted at a temperature of between 25° and 100° C.

31. A process for preparing the compound of claim 1 which comprises contacting a silane of the formula

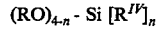

wherein R and $n$ have the meaning given in claim 1 and $R^{IV}$ represents a straight-chained or branched alkenyl group of 2 to 8 carbon atoms or a cycloalkenyl group of 5 to 6 carbon atoms with a compound of the formula

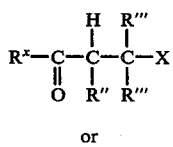

wherein R" and R'" have the meaning given in claim 1.

32. A process according to claim 31 wherein the silane is a compound selected from the group consisting of vinyltrimethoxysilane, allyltrimethoxysilane and butene-(3)-yl-trimethoxysilane.

33. A process according to claim 31 wherein the silane is contacted with a compound selected from the group consisting of acrolein, methacrolein and crotonic aldehyde.

34. A process according to claim 31 wherein the process is conducted in the presence of UV rays or another radical forming agent.

35. A process according to claim 34 wherein the radical forming agent is selected from the group consisting of dibenzoyl peroxide, diacetyl peroxide and di-tert.-butyl peroxide.

36. A process for preparing the compound of claim 1 which comprises contacting a silane of the formula

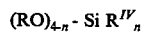

$$(RO)_{4-n}\text{-}Si\,R^{IV}_n$$

wherein R and n have the meaning given in claim 1 and $R^{IV}$ represents a straight-chained or branched alkyl group of 2 to 8 carbon atoms or a cycloalkenyl group of 5 to 6 carbon atoms, with a compound having the formula

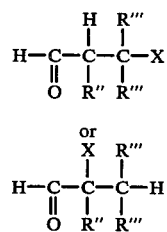

$$\begin{array}{c}H\quad R'''\\|\quad\;\;|\\H-C-C-C-X\\\|\quad|\quad|\\O\quad R''\;R'''\end{array}$$

or $$\begin{array}{c}X\quad R'''\\|\quad\;\;|\\H-C-C-C-H\\\|\quad|\quad|\\O\quad R''\;R'''\end{array}$$

wherein R'' and R''' have the meaning given in claim 1 and X is a halogen atom, a tertiary amine or acetyl group in the presence of a radical forming agent to form an intermediate and thereafter subjecting said intermediate compound to HX cleavage conditions.

37. A process according to claim 36 wherein said HX cleavage conditions comprise contacting the intermediate compound with an alkaline substance selected from the group consisting of an alkali metal $C_{1-8}$ alcoholate, an alkali metal phenolate or an amine selected from the group consisting of dicyclohexylethylamine, dicyclohexylmethylamine, diethylaniline and dimethylaniline.

38. A process according to claim 37 wherein the cleavage is conducted at a temperature of between 25° and 100° C.

39. A process according to claim 37 wherein the silane is contacted with a compound selected from the group consisting of 3-chloropropanal-1, 2-chloropropanal(1) and 3-chloro-2-methylpropanal(1).

40. A process according to claim 39 wherein the addition reaction is conducted in the presence of an inert liquid hydrocarbon.

41. A process according to claim 40 wherein said hydrocarbon is hexane or benzene.

42. A process according to claim 39 wherein the addition reaction is performed in the presence of a polymerization inhibitor.

43. A process according to claim 42 wherein said polymerization inhibitor is an aminophenol or hydroquinone.

44. A process for preparing the compound of claim 1 which comprises:

A. contacting a compound of the formula

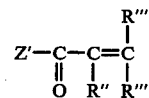

$$\begin{array}{c}R'''\\|\\Z'-C-C=C\\\|\quad|\quad|\\O\quad R''\;R'''\end{array}$$

wherein R'' and R''' have the meaning given in claim 1 and Z' is a halogen atom with a silane of the formula

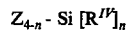

$$Z_{4-n}\text{-}Si\,[R^{IV}]_n$$

wherein n is 1 or 2, $R^{IV}$ represents a straight-chained or branched alkenyl group of 2 to 8 carbon atoms or a cycloalkenyl group of 5 to 6 carbon atoms and Z is halogen or an alkoxy group in the presence of a Friedel-Crafts catalyst to prepare a β-halogen ketone intermediate compound, and B. contacting β-halogen ketone intermediate compound with an alkanol, cycloalkanol, alkyloxyalkanol or phenol under esterification conditions to obtain an esterified β-halogen ketone.

45. A process according to claim 44 wherein the reaction of paragraph A is conducted at a temperature of between −10° and +20° C.

46. A process according to claim 45 wherein the Friedel-Crafts catalyst is selected from the group consisting of alumina chloride, tin(IV) chloride, zinc chloride and titanium chloride.

47. A process according to claim 46 wherein step A is conducted in the presence of a solvent selected from the group consisting of dichloromethane, carbontetrachloride, hexane and heptane.

48. A process for preparing the compound of claim 1 which comprises:

A. contacting a compound of the formula

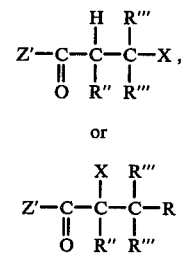

$$\begin{array}{c}H\quad R'''\\|\quad\;\;|\\Z'-C-C-C-X,\\\|\quad|\quad|\\O\quad R''\;R'''\end{array}$$

or $$\begin{array}{c}X\quad R'''\\|\quad\;\;|\\Z'-C-C-C-R\\\|\quad|\quad|\\O\quad R''\;R'''\end{array}$$

wherein R'' and R''' have the meaning given in claim 1, Z' is a halogen atom and X is a halogen, a tertiary amine or an acetyl group, with a compound of the formula

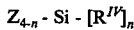

$$Z_{4-n}\text{-}Si\text{-}[R^{IV}]_n$$

wherein n is 1 or 2, $R^{IV}$ represents a straight-chained or branched alkenyl group of 2 to 8 carbon atoms or a cycloalkenyl group of 5 to 6 carbon atoms and Z is halogen or an alkoxy group in the presence of a Friedel-Crafts catalyst to prepare the corresponding α or β-halogen ketone intermediate compound.

B. contacting said α or β-halogen ketone intermediate compound with an alkanol, cycloalkanol, alkyloxyalkanol or phenol under esterification conditions to obtain an intermediate esterified α or β-containing halogen ketone; and C. subjecting the intermediate from step B to HX cleavage conditions.

49. A process according to claim 48 wherein the reaction of step A is conducted at a temperature of between −10° and +20° C.

50. A process according to claim 49 wherein the Friedel-Crafts catalyst is selected from the group consisting of aluminum chloride, tin(IV) chloride, zinc chloride and titanium chloride.

51. A process according to claim 50 wherein the HX cleavage conditions comprise contacting the intermediate from step B with an alkali metal $C_1$-$C_8$ alcoholate, an alkali metal phenolate, dicyclohexylmethylamine, dicyclohexylethylamine, diethylamine and dimethylaniline.

52. A process according to claim 48 wherein step C is carried out at a temperature of between 25° and 100° C.

53. A compound of the formula

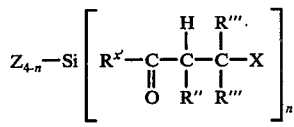

wherein Z is halogen or an alkoxy group,
$R^x$ represents a halogenated $C_2$-$C_8$ alkyl cycloalkyl or branched alkyl radical having at least one double or triple bond in the chain,
R'' is a halogen atom or an alkyl group having 1 to 4 carbon atoms,
R''' is a hydrogen atom, a straight-chained or branched alkyl or alkenyl group having 1 to 6 carbon atoms or a cycloalkyl group,
X is a halogen, a tertiary amine group or an acetyl group,
$n$ is 1 or 2.

54. A compound of the formula

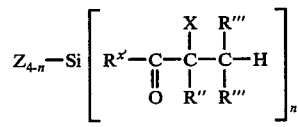

wherein Z is halogen or an alkoxy group,
$R^x$ represents a halogenated $C_2$-$C_8$ alkyl cycloalkyl or branched alkyl radical having at least one double or triple bond in the chain,
R'' is a halogen atom or an alkyl group having 1 to 4 carbon atoms,
R''' is a hydrogen atom or straight-chained or branched alkyl or alkenyl group having 1 to 6 carbon atoms or a cycloalkyl group,
X is a halogen, a tertiary amine group or an acetyl group.
$n$ is 1 or 2.

* * * * *

UNITED STATES PATENT AND TRADEMARK OFFICE
CERTIFICATE OF CORRECTION

PATENT NO. : 4,083,861
DATED : April 11, 1978
INVENTOR(S) : CLAUS DIETRICH SEILER et al It is certified that error appears in the above-identified patent and that said Letters Patent are hereby corrected as shown below:

Column 3, line 66, "preparation" should read -- separation --.

Column 9, line 10, "therefore" should read -- thereafter --.

Column 9, line 39, "uon" should read -- upon --.

Column 16, line 28, " Γ " should read -- γ --.

Column 22, line 45, "-R" should read -- -H --.

Signed and Sealed this

Fifteenth Day of August 1978

[SEAL]

Attest:

RUTH C. MASON
Attesting Officer

DONALD W. BANNER
Commissioner of Patents and Trademarks